US008983579B2

(12) United States Patent
Martz

(10) Patent No.: US 8,983,579 B2
(45) Date of Patent: Mar. 17, 2015

(54) SYRINGE WITH VISUAL USE INDICATOR

(71) Applicant: Mallinckrodt LLC, Hazelwood, MO (US)

(72) Inventor: Kevin R. Martz, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 16 days.

(21) Appl. No.: 13/794,141

(22) Filed: Mar. 11, 2013

(65) Prior Publication Data

US 2013/0190617 A1    Jul. 25, 2013

Related U.S. Application Data

(62) Division of application No. 13/133,290, filed as application No. PCT/US2010/023127 on Feb. 4, 2010, now Pat. No. 8,417,320.

(60) Provisional application No. 61/149,720, filed on Feb. 4, 2009.

(51) Int. Cl.
*A61M 5/00* (2006.01)
*A61M 5/145* (2006.01)
*A61M 5/31* (2006.01)
*A61M 5/50* (2006.01)
*A61B 6/00* (2006.01)

(52) U.S. Cl.
CPC ............ *A61M 5/007* (2013.01); *A61M 5/14546* (2013.01); *A61M 5/3129* (2013.01); *A61M 5/5086* (2013.01); *A61M 2205/0227* (2013.01); *A61M 2205/273* (2013.01); *A61M 2205/3331* (2013.01); *A61M 2205/583* (2013.01); *A61M 2205/587* (2013.01); *A61B 6/548* (2013.01)
USPC .......................................... 600/432; 604/187

(58) Field of Classification Search
USPC ............ 600/37, 432; 604/113, 131, 151–155, 604/82, 65–67, 187, 207, 500
See application file for complete search history.

(56) References Cited

U.S. PATENT DOCUMENTS

| 4,064,879 | A | 12/1977 | Leibinsohn |
| 4,292,916 | A | 10/1981 | Bradley et al. |
| 7,569,185 | B2 | 8/2009 | Fischer |
| 7,854,726 | B2 | 12/2010 | Fago et al. |
| 2007/0235083 | A1 | 10/2007 | Dlugos |
| 2007/0265567 | A1 | 11/2007 | Felix-Faure |
| 2008/0015406 | A1 | 1/2008 | Dlugos et al. |

FOREIGN PATENT DOCUMENTS

| FR | 2347058 | 11/1977 |
| WO | 0152919 | 7/2001 |
| WO | 2004057959 | 7/2004 |
| WO | 2007050281 | 5/2007 |
| WO | 2007075839 | 7/2007 |

*Primary Examiner* — Michael Rozanski
(74) *Attorney, Agent, or Firm* — James L. Johnson; Marsh Fischmann & Breyfogle LLP

(57) ABSTRACT

Systems and methods are presented for the visual indication of whether a power injector has discharged fluid from a power injector syringe in a previous medical procedure. In this regard, the systems and methods generally provide for a power injector and a syringe for use with the power injector. The syringe includes a visual indicator that moves between a first state and a second state at approximately the same time that the power injector discharges fluid from the syringe such that an operator may view the change in state.

22 Claims, 16 Drawing Sheets

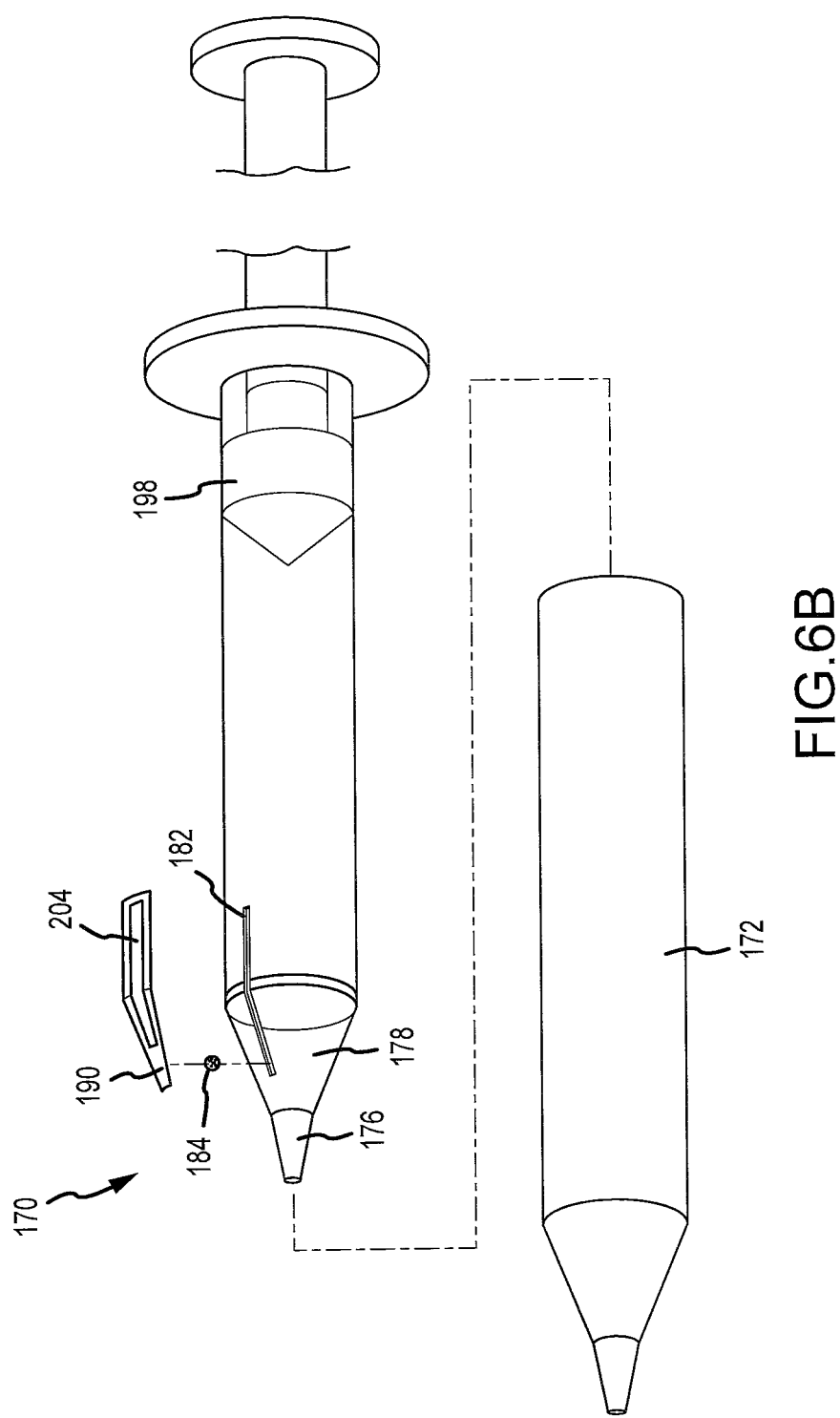

SYRINGE WITH VISUAL USE INDICATOR

RELATED APPLICATIONS

This application is a divisional of U.S. patent application Ser. No. 13/133,290, filed 7 Jun. 2011, now U.S. Pat. No. 8,417,320, which is a U.S. National Stage of PCT/US2010/023127, filed 4 Feb. 2010, which is a non-provisional of and claims priority to U.S. Provisional Patent Application No. 61/149,720 filed on 4 Feb. 2009 and entitled "SYRINGE WITH VISUAL USE INDICATOR". Priority is claimed to each patent application set forth in this Related Applications section.

FIELD OF THE INVENTION

The present invention generally relates to the field of syringes and, more particularly, to providing information that fluid may have previously been discharged from a syringe.

BACKGROUND

Various medical procedures require that one or more medical fluids be injected into a patient. For example, medical imaging procedures oftentimes involve the injection of contrast media into a patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe driver that is incorporated into the powerhead, such that operation of the syringe driver axially advances the associated syringe plunger inside and relative to a barrel of the syringe. One typical syringe driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Power injector syringes may be disposable—only used for a single injection. If a power injector syringe were to be re-used, it should be sterilized before being reloaded with fluid for use in a subsequent injection.

SUMMARY

As used herein, the phrase "fluidly isolated" or the like describes a relationship between components where fluid is not able to flow between the components. For example, where two components are fluidly isolated from each other, fluid is currently unable to flow from one component to the other component. Such an inability to flow may be due to one or more valves being positioned to prevent such flow between the two components. Certain components may at all times be fluidly isolated from each other.

As used herein, the phrases "fluidly interconnected, "in fluid communication with," "fluidly communicates with," or the like each describes a relationship between components where fluid is currently able to flow between the components. Such an inability to flow may be due to one or more valves being positioned to allow such flow between the two components. Certain components may at all times be in fluid communication with each other. For example, "an injection device fluidly interconnected to a patient" describes a configuration where fluid is able to flow from the injection device, through any intermediate components (e.g., tubing, connectors), and to the patient (e.g., into the vasculature of the patient).

A first aspect of the present invention is embodied by a power injector that includes a syringe plunger driver and a syringe. The syringe plunger driver includes a plunger interface and a motorized drive source operable to move the plunger interface in multiple directions (e.g., in each direction along an axial path). The syringe includes an internal fluid discharge chamber, a syringe plunger that is movably disposed within this fluid discharge chamber, and a visual indicator member that is located outside of the fluid discharge chamber (e.g., on an exterior surface of the syringe). To discharge the syringe, the syringe plunger driver interacts with the syringe plunger to move the syringe plunger in at least a first direction. Prior to the advancement of the syringe plunger, the visual indicator member is in a first state, but the visual indicator member is irreversibly changed to a second state in response to the movement of the syringe plunger by the syringe plunger driver.

A number of feature refinements and additional features are applicable to the first aspect of the present invention. These feature refinements and additional features may be used individually or in any combination. The following discussion is applicable to the first aspect, up to the start of the discussion of a second aspect of the present invention.

The syringe may include a syringe body, where the syringe plunger is movable relative to the syringe body and where at least part of the syringe plunger (e.g., a plunger head) is disposed within the syringe body. To move the syringe plunger within the syringe body in at least a first axial direction, the syringe plunger driver may include an axially moveable ram, and the plunger interface may move along with the ram. In turn, the plunger interface interacts with the syringe plunger to move it in at least one axial direction. The plunger interface may be of any appropriate size, shape, configuration, and/or type to allow the syringe plunger driver to interact with the syringe plunger in any appropriate manner to move the syringe plunger in at least one axial direction (e.g., a mechanical coupling, magnetic coupling, etc.).

The visual indicator member may be disposed on an exterior of the syringe body such that the visual indicator member remains at all times isolated from any fluid contained within the syringe (e.g., fluid within the fluid discharge chamber). For instance, the visual indicator member may be disposed between the syringe body and a label attached to an exterior of the syringe body. To allow an operator to observe the visual indicator member, the label may include at least one transparent section that coincides with the visual indicator member such that the visual indicator member is visible through the transparent section. The transparent section may be a discrete portion of the label or it may coincide with the entirety of the label, and the transparent section may be formed of any material that accommodates viewing a visual change through the transparent section. For example, the transparent section may be clear or of translucent color so long as an operator may perceive a visual change through the transparent section.

The visual indicator member itself may be in the form of a pressure-sensitive material. This pressure-sensitive material may include any material that exhibits an optically detectable response to changes in pressure (e.g., a pressure-sensitive adhesive, polymer, gel, foam, etc.). For example, the pressure-sensitive material may take the form of a label adhesive, a separate material that is disposed between a label and the syringe body, or it may be incorporated into the label itself. When disposed outside of the fluid discharge chamber (e.g., on an exterior of the syringe body), the pressure-sensitive material may change from a first color to a second color in response to exposure to a pressure change. Thus, as the syringe plunger advances in a direction to discharge fluid from the syringe, the pressure within the syringe body increases, thereby causing the pressure-sensitive material to change from a first state (e.g., a first color) to a second state (e.g., a second color).

The visual indicator member could also be in the form of a fluid source. The fluid source may include a first fluid within an enclosure. The first fluid may be any visible indicator fluid (e.g., a colored fluid, for instance a liquid) of an appropriate viscosity that allows the indicator fluid to flow, and the enclosure may be formed of any deformable, malleable, and/or rupturable material that ruptures upon exposure to at least a certain pressure (e.g., a blister pack).

The visual indicator member may further include a flowpath that is interconnectable with the fluid source. The flowpath may be configured such that the first fluid and the flowpath are fluidly isolated when the visual indicator member is in a first state (i.e., before the fluid source ruptures), but that the first fluid flows within the flowpath when the visual indicator member is in a second state (i.e., after the fluid source ruptures). The flowpath may be a channel that is inset into or fully enclosed within the exterior of the syringe and that recedes from the fluid source. The channel may be of any appropriate size, shape, and/or configuration to allow fluid to flow within it along a visible portion of the syringe body (e.g., at least about 10% of a length of the syringe body). In addition, a label may be disposed over the flowpath (such that the first fluid is contained between the label and an exterior of the syringe). To allow an operator to observe the visual indicator member, the label may include at least one transparent section that coincides with the visual indicator member such that the visual indicator member is visible through the transparent section. The transparent section may be a discrete portion of the label or it may coincide with the entirety of the label, and the transparent section may be formed of any material that accommodates viewing a visual change through the transparent section. For example, the transparent section may be clear or of translucent color so long as an operator may perceive a visual change through the transparent section.

In one embodiment, the fluid source may be aligned with a moveable member. This movable member may be incorporated into the structure of the syringe. For instance, the moveable member may be a dimple, a hollow, or a depression in the surface of the syringe that may be of any appropriate size, shape, and/or configuration to receive the fluid source. In a first position, the moveable member may be convex in relation to the interior of the syringe and concave in relation to the exterior of the syringe. In a second position, the moveable member may be convex in relation to the exterior of the syringe and concave in relation to the interior of the syringe. The moveable member may move between the first and second positions, or invert, in response to a pressure increase in the interior of the syringe that develops within the syringe as the syringe plunger advances in a direction to discharge fluid from the syringe. This inversion, or movement between the first and second positions, may compress the fluid source between the moveable member and another structure (e.g., an overlying label), thereby causing the fluid source to rupture and release the indicator fluid to flow down the flowpath and serve as a visual indicator that the power injector has discharged fluid from the syringe.

In one embodiment, the syringe may be disposed within a pressure jacket that is configured to restrain the syringe body when the syringe is pressurized. The pressure jacket may be of any appropriate size, shape, configuration, and/or type to fully encompass the syringe body and withstand a certain amount of outward force from the pressurized syringe so as to prevent the pressurized syringe from rupturing when fully pressurized by the power injector. In this embodiment, the moveable member may be a deformable, frustumly-shaped section of the syringe located between a syringe barrel and a discharge port of the syringe body. The fluid source may be disposed upon the frustumly-shaped surface between the exterior surface of the syringe and a corresponding interior surface of the pressure jacket. As the syringe plunger driver advances the syringe plunger in a direction to discharge fluid from the syringe, the moveable member may deform and/or the syringe may move axially relative to the pressure jacket in response to a pressure increase that develops within the syringe. This deformation and/or syringe movement may compress the fluid source between the exterior surface of the syringe and the interior surface of the pressure jacket, which may rupture the fluid source and release the indicator fluid to flow along the flow path.

A second aspect of the present invention is embodied by a power injector that includes a syringe plunger driver, a light source, and a syringe. The syringe plunger driver includes a plunger interface and a motorized drive source that is operable to move the plunger interface in multiple directions (e.g., in each direction along an axial path). The syringe includes a syringe plunger and a visual indicator member that irreversibly changes between a first state and a second state in response to the activation of the light source.

A third aspect of the present invention is embodied by a method of operation for a power injector. This method includes the steps of exposing a visual indicator member on a syringe to an output from a light source in order to change the color of the visual indicator, and advancing a ram to in turn advance a syringe plunger.

A number of feature refinements and additional features are applicable to the second and third aspects of the present invention. These feature refinements and additional features may be used individually or in any combination. The following discussion is applicable to the second and third aspects, up to the start of the discussion of a fourth aspect of the present invention.

The light source may be of any appropriate type, and may issue light of any appropriate wavelength or combination of wavelengths (e.g., ultra violet ("UV") light). Operation of the light source could be controlled by the power injector, the light source could be manually activated (e.g., by a clinician), or both. The light source may be incorporated by the power injector in any appropriate manner. For instance, the power injector may include a powerhead of any appropriate size, shape, configuration, and/or type, and the light source could be integrated into the structure of the powerhead. The light source could also be detachably mounted to the power injector in any appropriate manner and at any appropriate location. In one embodiment, the light source is a handheld unit and may be manually operated.

The visual indicator member may be disposed on an exterior of the syringe such that the visual indicator member remains at all times fluidly isolated from any fluid contained within the syringe. For instance, the visual indicator member may be disposed between the syringe body and a label. To allow an operator to observe the visual indicator member, the label may include at least one transparent section that coincides with the visual indicator member such that the visual indicator member is visible through the transparent section. The transparent section may be a discrete portion of the label or it may coincide with the entirety of the label, and the transparent section may be formed of any material that accommodates viewing a visual change through the transparent section. For instance, the transparent section may be clear or have a translucent color that allows an operator may perceive a visual change through the transparent section.

The visual indicator member itself may be formed of any appropriate light-sensitive material that exhibits an optically detectable response to exposure to at least certain light (e.g., UV-sensitive adhesives, gels, foams, paints, etc.). For example, the light-sensitive material may take the form of a label adhesive, a separate material that is disposed beneath the label, or it may be incorporated into the structure of the label itself. When disposed on the exterior of the syringe body, the visual indicator member may change from a first color to a second color upon exposure to at least a certain light, thereby providing a visual indication to an operator that the power injector has discharged fluid from the syringe.

The light exposure may occur either before or after advancement of the syringe plunger to discharge fluid from the syringe. In addition, an operator may manually initiate exposure or exposure may be integrated with an injection or operations protocol such that exposure occurs automatically at the appropriate time.

A fourth aspect of the present invention is embodied by a syringe. Components of the syringe include a syringe body having an interior surface and an exterior surface, a syringe plunger moveably disposed within the syringe body, a label disposed on the exterior surface of the syringe body, and a pressure-sensitive material disposed between the label and the exterior surface of the syringe body.

A number of feature refinements and additional features are applicable to the fourth aspect of the present invention. These feature refinements and additional features may be used individually or in any combination. The following discussion is applicable to the fourth aspect, up to the start of the discussion of a fifth aspect of the present invention.

The syringe plunger may have a proximal end that includes a coupling adapted to interact with a syringe plunger driver of a power injector. The power injector may be any appropriate power injector adapted for use with a syringe, and the coupling may be of any appropriate size, shape, configuration, and/or type to allow the syringe plunger driver to interact with the syringe plunger to move the syringe plunger in at least one direction.

To allow an operator to observe the pressure-sensitive material, the label may be disposed on the exterior surface of the syringe body, and furthermore may include at least one transparent section that coincides with the pressure-sensitive material such that the material is visible through the transparent section. The transparent section may be a discrete portion of the label or it may coincide with the entirety of the label, and the transparent section may be formed of any material that accommodates viewing a visual change through the transparent section. For instance, the transparent section may be clear or of translucent color so long as an operator may perceive a visual change through the transparent section.

The pressure-sensitive material itself may be any material that exhibits an optically detectable response to changes in pressure (e.g., a pressure-sensitive adhesive, polymer, gel, foam, etc.). For example, the pressure-sensitive material may take the form of a label adhesive or of another, separate material that is disposed beneath the label. When disposed between the label and the exterior surface of the syringe body, the pressure-sensitive material may change from a first color to a second color in response to a pressure change. That is, prior to exposure to at least a first pressure, the pressure-sensitive material is in a first sate (e.g., a first color), and after exposure to at least a first pressure, the pressure-sensitive material is irreversibly changed to a second state (e.g., a second color).

A fifth aspect of the present invention is embodied by a syringe having a syringe body, which in turn includes an internal fluid discharge chamber. The syringe further includes a syringe plunger that movably disposed within the syringe body (e.g., within the fluid discharge chamber), a fluid source that is disposed outside of the fluid discharge chamber, and a movable member aligned with the fluid source.

A sixth aspect of the present invention is embodied by a method for operating a power injector. The method includes the steps of advancing a ram to advance a syringe plunger of a syringe, expanding a first portion of the syringe in response to a differential pressure created in the syringe as the syringe plunger advances, and activating a first visual indicator in response to this expansion of the syringe.

A number of feature refinements and additional features are applicable to the fifth and sixth aspects of the present invention. These feature refinements and additional features may be used individually or in any combination.

The first visual indicator may be a fluid source that includes a first fluid within an enclosure. The first fluid may be any visible indicator fluid (e.g., a colored liquid, etc.) of an appropriate viscosity that allows the indicator fluid to flow, and the enclosure may be formed of a deformable, malleable, and/or rupturable material that ruptures upon exposure to at least a certain pressure (e.g., a blister pack).

In addition, the syringe may include a flowpath that is fluidly interconnectable with the fluid source. The flowpath may be a channel that is inset into or fully enclosed on an exterior of the syringe body (e.g., so as to be fluidly isolated from an internal fluid discharge chamber of the syringe) and that extends from the fluid source down a visible portion of the syringe body (e.g., to at least about 10% down the length of the syringe body). In a first state (i.e., prior to an advancement of the syringe plunger to discharge fluid from the syringe body), the fluid source and the flowpath may be fluidly isolated, while in a second state (i.e., the development of a differential pressure in response to the advancement of the syringe plunger), the fluid source communicates with the flowpath. A label may be disposed over each of the fluid source and the channel. The label may include a transparent section that coincides with at least a portion of the channel. The transparent section may be a discrete portion of the label or it may coincide with the entirety of the label, and the transparent section may be formed of any material that accommodates viewing a visual change through the transparent section. For instance, the transparent section may be clear or of translucent color so long as an operator may perceive a visual change through the transparent section.

In one embodiment, the moveable member may be a dimple, a hollow, or a depression formed in the structure of the syringe. The moveable member may be of any appropriate size, shape, and/or configuration so as to receive the fluid source. In a first position and prior to the movement of the syringe plunger to discharge fluid from the syringe, the moveable member may be convex relative to the interior of the syringe and concave relative to the exterior of the syringe. As the syringe plunger advances to discharge fluid from the syringe body, a differential pressure develops. In response to this differential pressure, the moveable member may move from the first position to a second position (e.g., invert) such that the moveable member is now concave relative to the interior of the syringe and convex relative to the exterior of the syringe. The inversion, or movement of the moveable member between the first and second positions, may compress the fluid source between the moveable member and another structure (e.g., a label on an exterior of the syringe), thereby rupturing the fluid source and releasing the first fluid to flow along the flowpath where an operator may view the resulting color change through the transparent section of the label and know that fluid has been discharged fluid from the syringe. In one embodiment, the syringe may be disposed within a pressure jacket that is configured to restrain the syringe body when the syringe is pressurized. The pressure jacket may be of any appropriate size, shape, configuration, and/or type to fully encompass the syringe body and withstand a certain amount of outward force from the pressurized syringe so as to prevent the pressurized syringe from rupturing when fully pressurized. In this embodiment, the moveable member may be a deformable, frustumly-shaped section of the syringe located between a syringe barrel and a discharge port of the syringe body. The fluid source may coincide with the frustumly-shaped surface between the exterior surface of the syringe body and the pressure jacket.

As the syringe plunger advances to discharge fluid from the syringe body, the deformable section may distort outward and/or the syringe may move axially relative to the pressure jacket to compress the fluid source between the exterior surface of the syringe and an interior surface of the pressure jacket. As a result, the fluid source ruptures, and the indicator fluid flows down the flowpath where it is visible to an operator through the transparent portion of the label, thereby providing a visual indication that the power injector has discharged fluid from the syringe.

A number of feature refinements and additional features are separately applicable to each of above-noted first, second, third, fourth, fifth, and sixth aspects of the present invention. These feature refinements and additional features may be used individually or in any combination in relation to each of the above-noted first, second, third, fourth, fifth, and sixth aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient, for instance for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

The syringes disclosed herein may be used with power injectors as noted. However, these syringes may be used with other types of injection devices. For instance, these syringes may be used with a hand-held, hand-powered syringe having a pair of levers that are movably interconnected (e.g., by a pivot pin), where one lever is also movably interconnected with the syringe body (e.g., by a pivot pin), and where the other lever is movably interconnected with the plunger (e.g., by a pivot pin) such that that a single hand of a user may engage and manipulate the levers to change the position of the plunger relative to the syringe body. Although any appropriate pressure could trigger the visual indication discussed herein, in one embodiment the trigger pressure is of a more elevated level such that these syringes may be suited for fluid delivery devices that are capable of generating elevated pressures.

BRIEF DESCRIPTION OF THE FIGURES

FIG. 6B is an exploded perspective view of the syringe of FIG. 6A.

DETAILED DESCRIPTION

Figure 1:
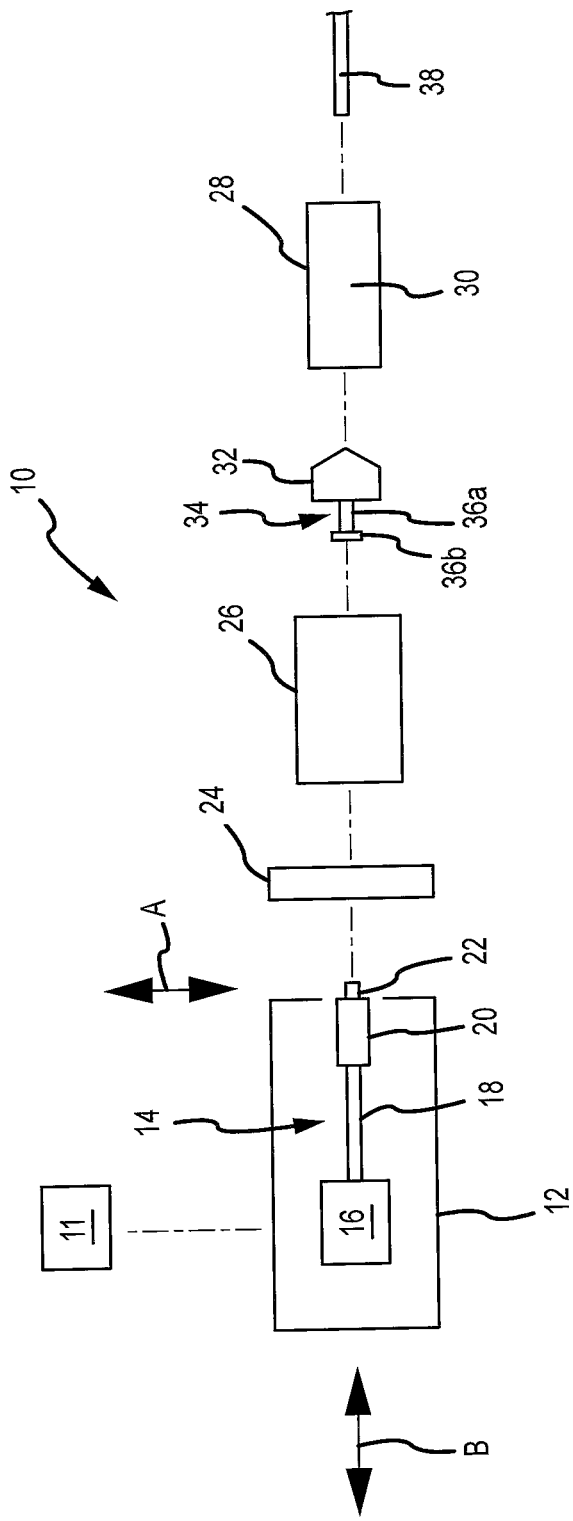
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
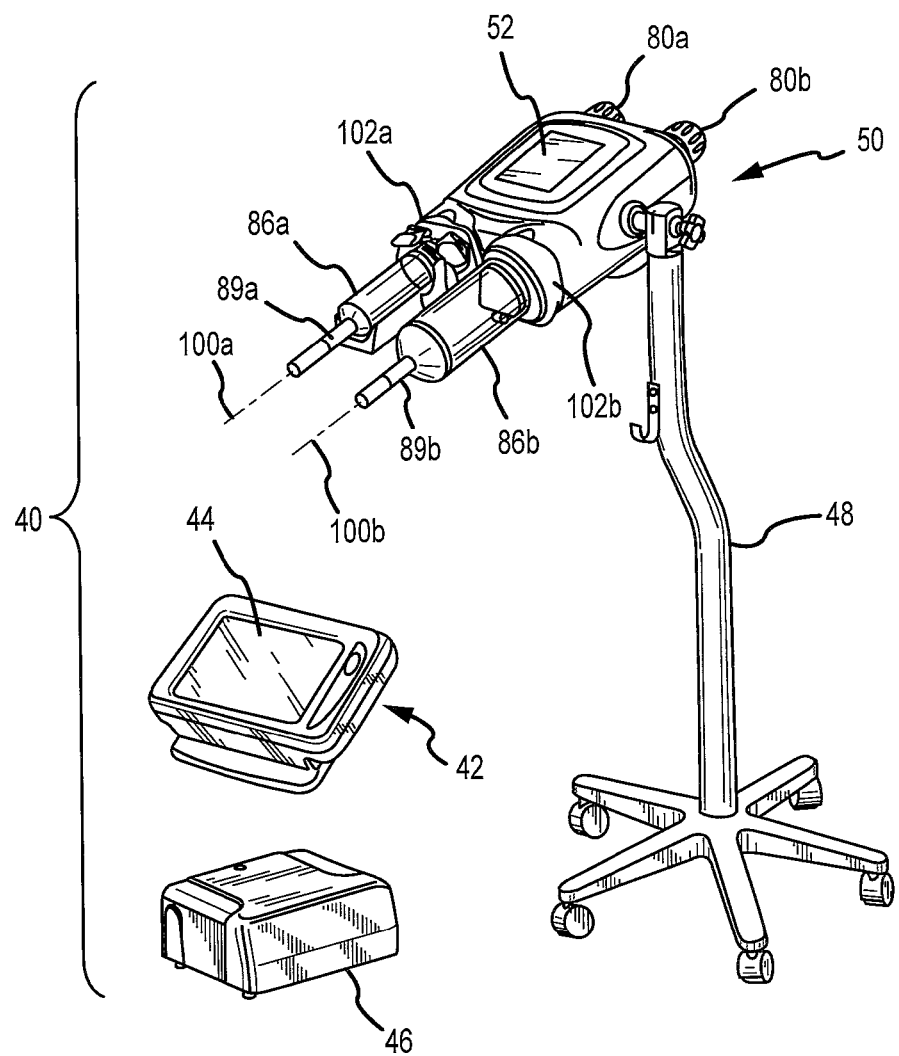
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
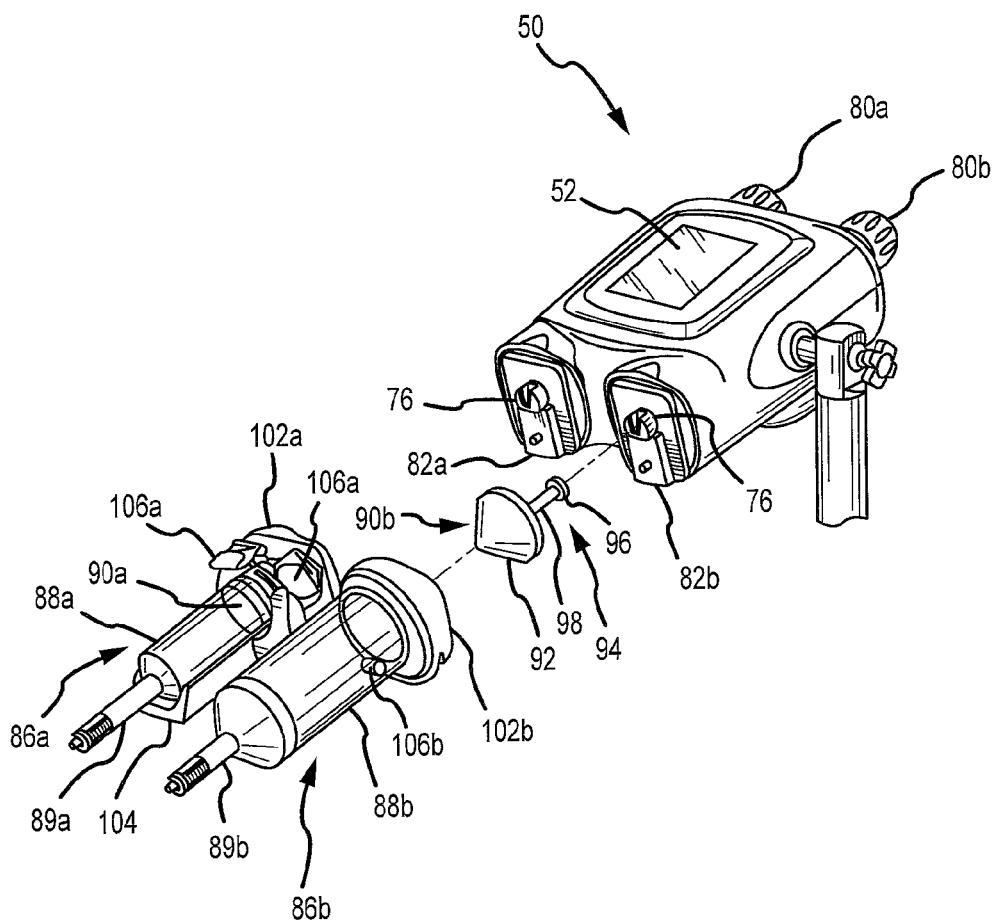
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
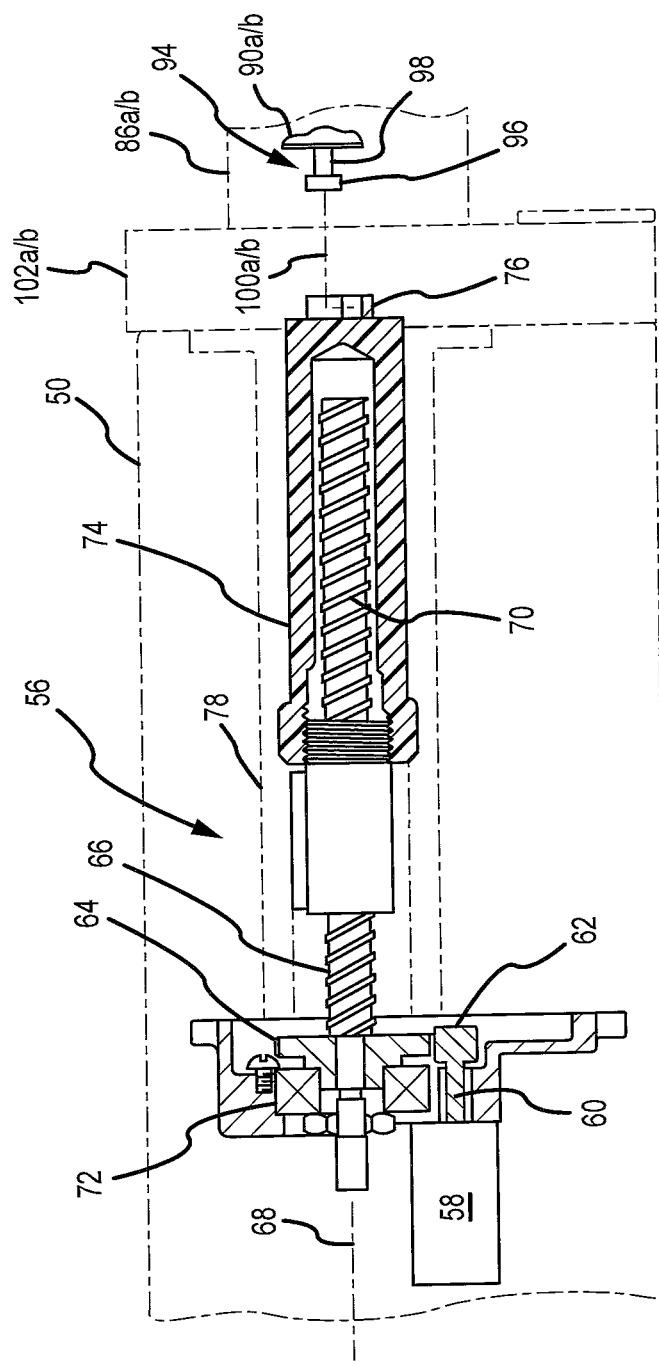
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
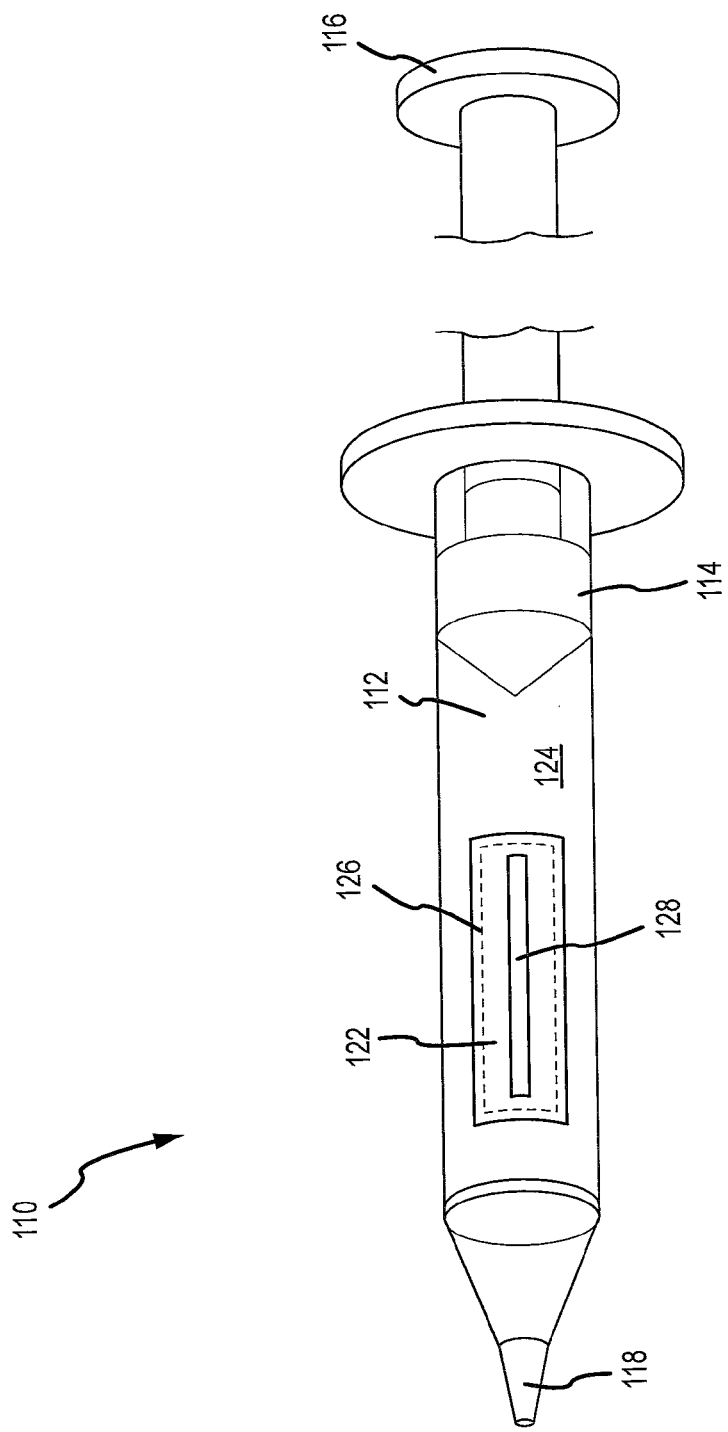
FIG. 3 is a perspective view of a syringe that utilizes one embodiment of a visual indicator.
Figure 4A:
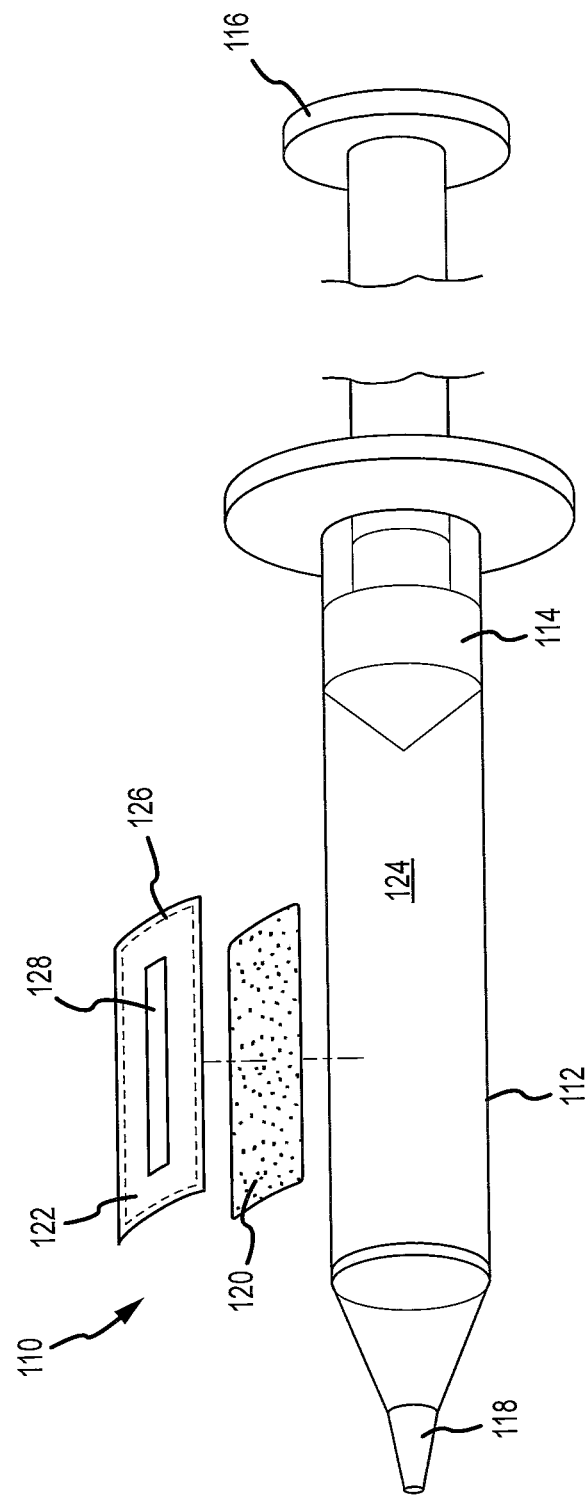
FIG. 4A is an exploded perspective view of the syringe of FIG. 3.
Figure 4B:
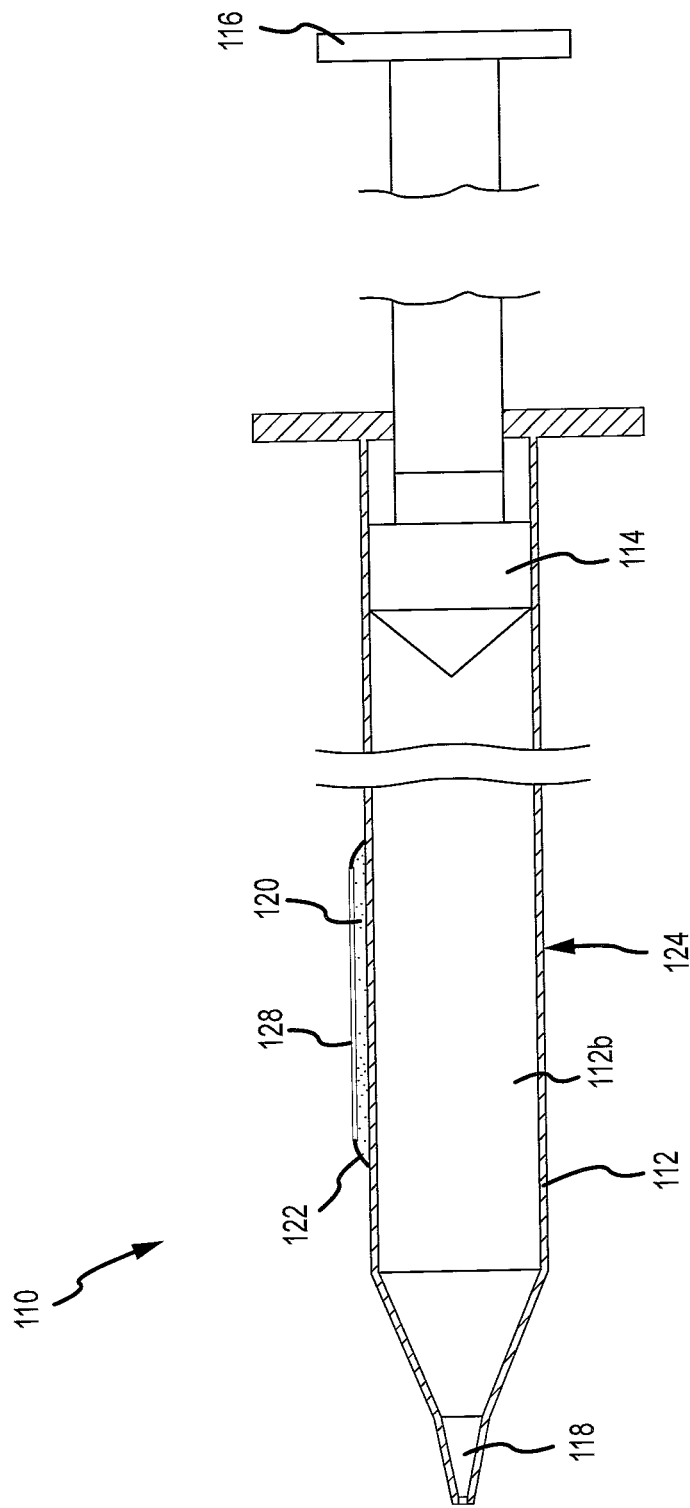
FIG. 4B is a cross-sectional view of the syringe of FIG. 3.

FIGS. 3 and 4A-B illustrate one embodiment of a syringe 110 that may be used in connection with a power injector or any other appropriate injection device. Hereafter, the syringe 110 will be described in conjunction with the power injector 40 (FIGS. 2A-C), although it should be appreciated that the syringe 110 may be used with any appropriate power injector (e.g., the power injector 10 of FIG. 1). Generally, the syringe 110 is adapted to provide a clear visual indication that fluid has likely been discharged from the syringe 110 in a previous medical procedure so as to reduce the potential of syringe 110 being reused. Medical professionals seek to avoid mistakenly reusing syringes, because once a syringe has been discharged in connection with a patient, it may be unsanitary to reuse that syringe with respect to another patient or even to reuse it for another medical procedure with respect to the same patient without first sterilizing the syringe 110.

In this embodiment, syringe 110 includes a syringe body 112 having an internal fluid discharge chamber 112a and a nozzle 118. A plunger 114 is movably disposed within the syringe body 112 and may include a syringe plunger coupler 116 (e.g., for interacting with an injection device). To discharge fluid through the nozzle 118, the syringe plunger coupler 116 may interact with the syringe plunger drive assembly 56 (FIG. 2C) of the power injector 40 (FIGS. 2A-C) so as to advance the syringe plunger 114 relative to the syringe body 112 (e.g., to advance the syringe plunger 114 through the fluid discharge chamber 112a). Using the power injector 40 to discharge the syringe 110 in this manner may result in a relatively high pressure being generated within the syringe 110. In this regard, a section of pressure-sensitive material 120 may be disposed between an exterior surface 124 of the syringe body 112 and a label 122 that is appropriately attached to the exterior surface 124 of the syringe body 112 (e.g., such that the pressure-sensitive material 120 is fluidly isolated from the internal fluid discharge chamber 112a). The pressure-sensitive material 120 may be in the form of any material that exhibits an optically detectable response to changes in pressure (e.g., pressure-sensitive adhesive, polymer, gel, foam, etc.), such that the section of pressure-sensitive material 120 moves or changes from a first state to a second state in response to any appropriate level of pressurization of the syringe body 112. For example, the section of pressure-sensitive material 120 may change from a first color to a second color when the power injector 40 (FIGS. 2A-C) pressurizes the syringe body 112 (e.g., develops an internal pressure of at least 15 psi within the syringe body 112).

In one embodiment, the label 122 may be of any appropriate size or shape that is sufficient to fully contain the section of pressure-sensitive material 120 between the label 122 and the exterior surface 124 of the syringe body 112. Specifically, beyond an offset perimeter 126, shown in FIG. 3, the label 122 may affix directly to the exterior surface 124 of the syringe body 112 so as to fully contain the section of pressure-sensitive material 120 beneath the label 122, as shown in FIGS. 4A-B. This approach reduces the potential that the section of pressure-sensitive material 120 will be exposed beyond the edge of the label 122. It should be appreciated, however, that some embodiments may not include the offset perimeter 126. For example, if the section of pressure-sensitive material 120 includes a pressure-sensitive adhesive that adheres the label 122 to the exterior surface 124 of the syringe body 112, then the section of pressure-sensitive material 120 may extend beneath the full area of the label 122.

The label 122 may also include a transparent portion 128 through which the section of pressure-sensitive material 120 is visible to an operator who may observe the section of pressure-sensitive material 120 both before and after the syringe 110 has been discharged. The transparent portion 128 may be of any appropriate shape or size to maximize visibility of the pressure-sensitive material 120.

Another embodiment of a syringe 140 for installation on and use with a power injector is illustrated in FIGS. 5A-E. Hereafter, the syringe 140 will be described in conjunction with the power injector 40 (FIGS. 2A-C) although it should be appreciated that the syringe 140 may be used with any appropriate power injector (e.g., the power injector 10 of FIG. 1) or any other appropriate injection device. In this embodiment, the syringe 140 includes a syringe body 142 and a nozzle 146 with a frustumly-shaped or conical transition portion 150 disposed between the syringe body 142 and the nozzle 146. A moveable dimple 152 is disposed on the conical transition portion 150, such that the moveable dimple 152 is convex relative to the inside of the conical transition portion 150 (and including in relation to the interior, fluid-containing volume of the syringe 140, or an internal fluid discharge chamber 142a). In addition, a channel or groove 156 may be inset into the conical transition portion 150 and the syringe body 142 (e.g., the channel 156 may be formed on the exterior of the syringe 140, or such that the channel 156 is otherwise fluidly isolated from the internal fluid discharge chamber 142a). The channel 156 recedes from the moveable dimple 152 of the conical transition portion 150 to the syringe body 142, and then extends along at least part of the length of the syringe body 142 (e.g., along at least about 10% of the length of the syringe body 142). An enclosed fluid source 158 (e.g., a blister pack) includes an amount of indicator fluid 164 encapsulated within a malleable, deformable, and/or rupturable enclosure 166. The enclosed fluid source 158 may be disposed within the moveable dimple 152 and below/underneath a label 148 that is configured to cover or enclose both the enclosed fluid source 158 and the entire length of the channel 156. The enclosure 166 may be formed of any appropriate substance that is sufficiently compliant so as to rupture upon exposure to a certain amount of pressure.

Figure 5A:
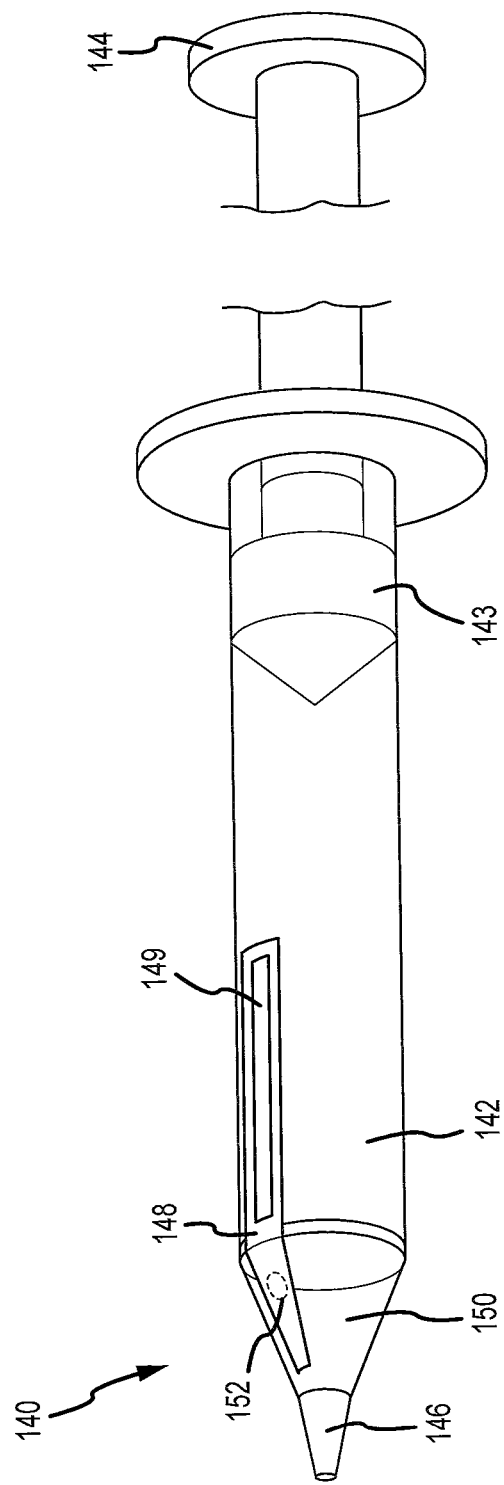
FIG. 5A is a perspective view of a syringe that utilizes another embodiment of a visual indicator.
Figure 5B:
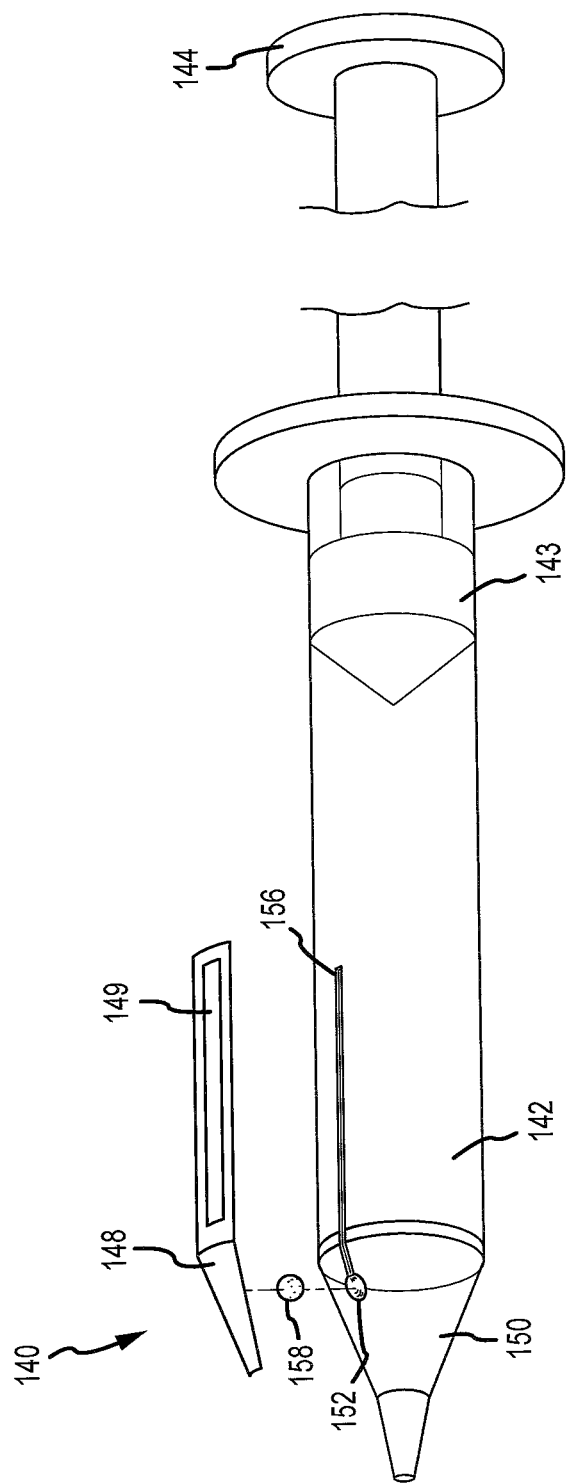
FIG. 5B is an exploded perspective view of the syringe of FIG. 5A.
Figure 5C:
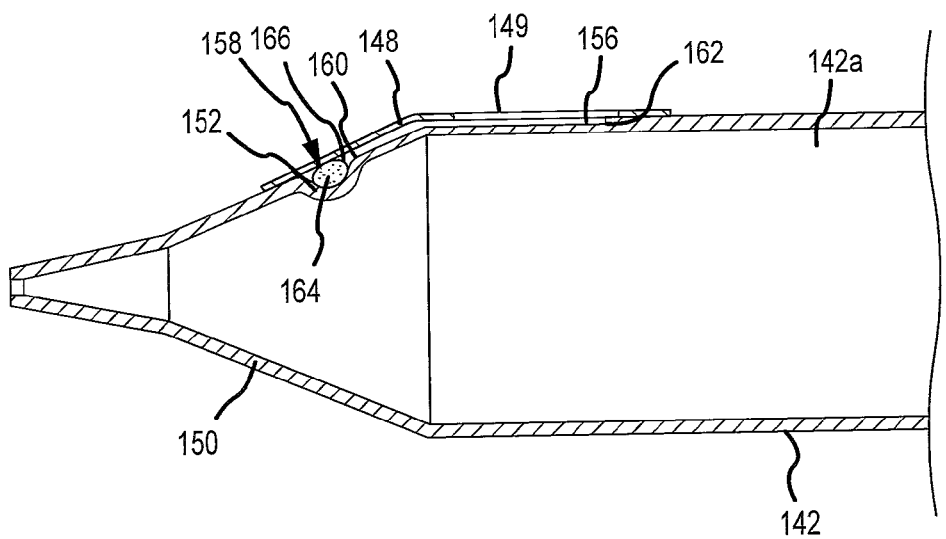
FIG. 5C is a partial, enlarged, cross-sectional view of the syringe of FIG. 5A in a first state.
Figure 5D:
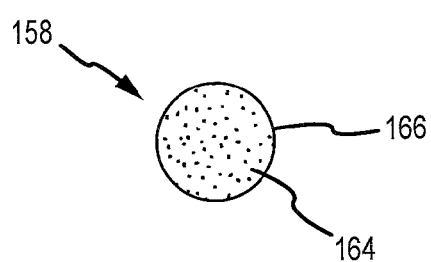
FIG. 5D is a detailed view of the fluid source.
Figure 5E:
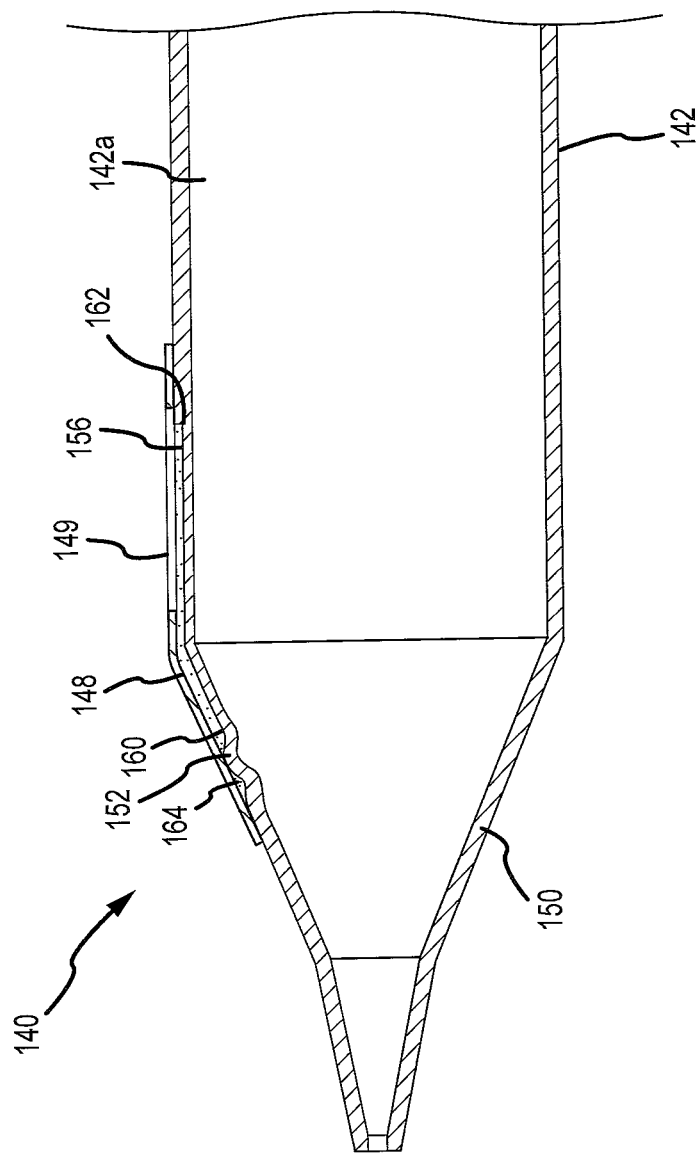
FIG. 5E is a partial, enlarged, cross-sectional view of the syringe of FIG. 5A in a second state.

Like the syringe 110 discussed above, the syringe 140 may interact with the syringe plunger driver assembly 56 (FIG. 2C) of the power injector 40 (FIGS. 2A-C) through a syringe plunger coupler 144 of the syringe plunger 143. When disposed in interacting relation, the syringe plunger driver assembly 56 (FIG. 2C) may advance the syringe plunger 143 relative to the syringe body 142 so as to discharge fluid from the nozzle 146. As the syringe plunger 143 advances, pressure builds within the syringe body 142 and inverts the moveable dimple 152 into a position where the dimple 152 may then be concave relative to the inside of the conical transition portion 150 (e.g., the interior of the syringe 140) and convex relative to the exterior of the syringe 140. This movement compresses the enclosed fluid source 158 between the moveable dimple 152 and the label 148 and causes the enclosed fluid source 158 to rupture, thereby releasing the indicator fluid 164 and allowing it to flow along the channel 156 from the moveable dimple 152 to a distal end 162 of the channel 156, as shown in FIGS. 5C and 5E.

In this embodiment, the label 148 may include a transparent portion 149 that extends at least from a proximal end 160 of the channel 156 to the distal end 162 of the channel 156, such that an operator may observe that indicator fluid 164 is present in the channel 156 and know that the syringe 140 has been previously discharged. To allow for prominent visual indication, the indicator fluid 164 may be any colored fluid of an appropriate viscosity that allows the indicator fluid 164 to flow along the channel 156.

In some instances, it may be unnecessary to dispose the enclosed fluid source 158 within a moveable dimple 152. In general and as discussed above with respect to FIG. 1, some injection procedures may result in a relatively high pressure being generated within the syringe. In this regard, a syringe may be disposed within a pressure jacket that protects the syringe from rupturing under pressure. The pressure jacket is typically associated with the powerhead of the power injector in a manner that allows a syringe to be disposed therein as a part of or after installing the syringe on the powerhead. One of ordinary skill in the art will understand that, generally, in instances where a pressure jacket is used in connection with the syringe, it may become unnecessary to dispose the enclosed fluid source or blister pack within a moveable dimple, as discussed above. Instead, the enclosed fluid source may be placed between the external surface of the syringe and the internal surface of the pressure jacket. When the syringe is pressurized, it deforms such that the enclosed fluid source is compressed between the exterior surface of the syringe and the interior surface of the pressure jacket and ruptures, thereby freeing the indicator fluid to flow along the channel. Such an embodiment is shown in FIGS. 6A-E.

In greater detail, FIGS. 6A-E illustrate another embodiment of a syringe 170 for use with a power injector. Hereafter, the syringe 170 will be described in conjunction with the power injector 40 (FIGS. 2A-C), although it should be appreciated that the syringe 170 may be used with any appropriate power injector (e.g., the power injector 10 of FIG. 1). In this embodiment, the syringe 170 is disposed within a pressure jacket 172. The syringe 170 includes a syringe body 174 and a nozzle 176 with a frustumly-shaped or conical transition portion 178 disposed between the syringe body 174 and the nozzle 176. A channel or groove 182 may be inset into the conical transition portion 178 and the syringe body 174 (e.g., the channel 182 may be formed on the exterior of the syringe 170, or such that the channel 182 is otherwise fluidly isolated from an internal fluid discharge chamber 174a). The channel 182 extends from a proximal end 192 (e.g., located at approximately a midpoint of the conical transition portion 178) to a distal end 206 (e.g., located at least about 10% down the length of the syringe body 174). The proximal end 192 of the channel 182 is configured to accommodate the diameter of an enclosed fluid source 184 (e.g., a blister pack). The enclosed fluid source 184 includes an amount of indicator fluid 186 encapsulated within a malleable, deformable, and/or rupturable enclosure 188. The enclosed fluid source 184 may be disposed at the proximal end 192 of the channel 182 such that it protrudes outward from the channel 182 to fill the gap 202 between the exterior of the conical transition portion 178 and an inside surface 194 of the pressure jacket 172. A label 190 may be disposed over the enclosed fluid source 184 and extend over the length of the channel 182. As discussed above, the enclosure 188 may be any appropriate substance that is sufficiently compliant so as to rupture upon the application of a certain amount of pressure.

Figure 6A:
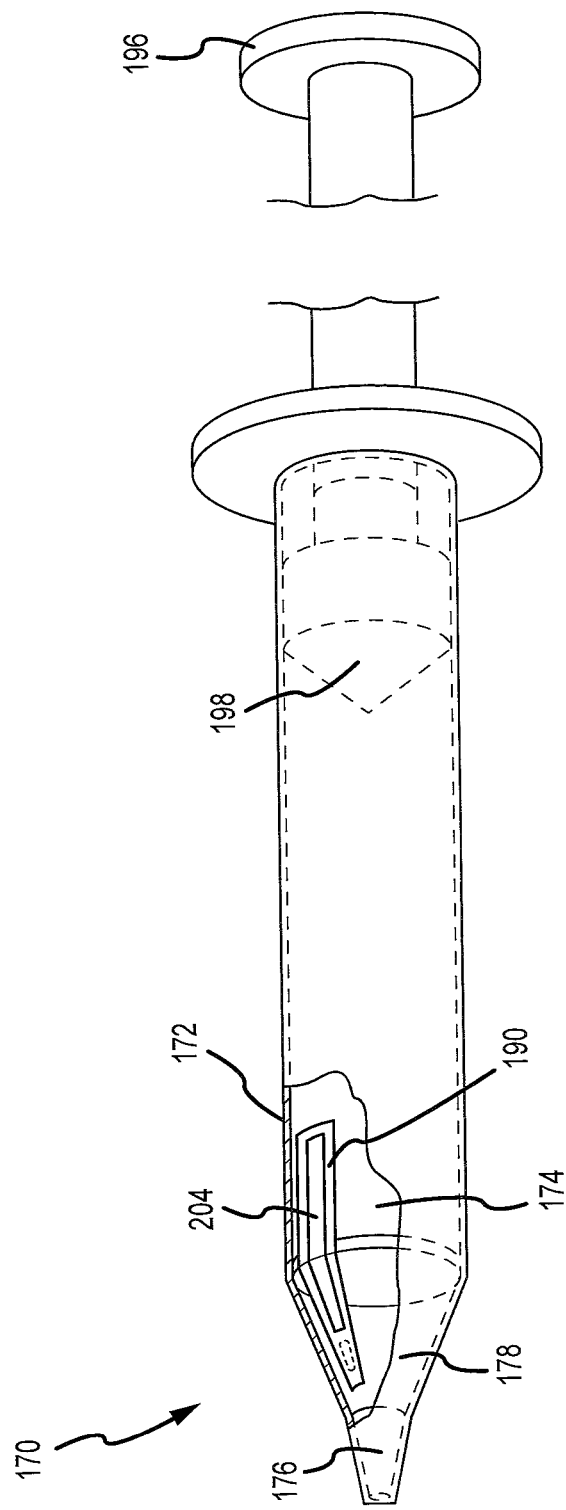
FIG. 6A is a perspective view of a syringe that utilizes another embodiment of a visual indicator, and that is used in conjunction with a pressure jacket on a power injector.
Figure 6C:
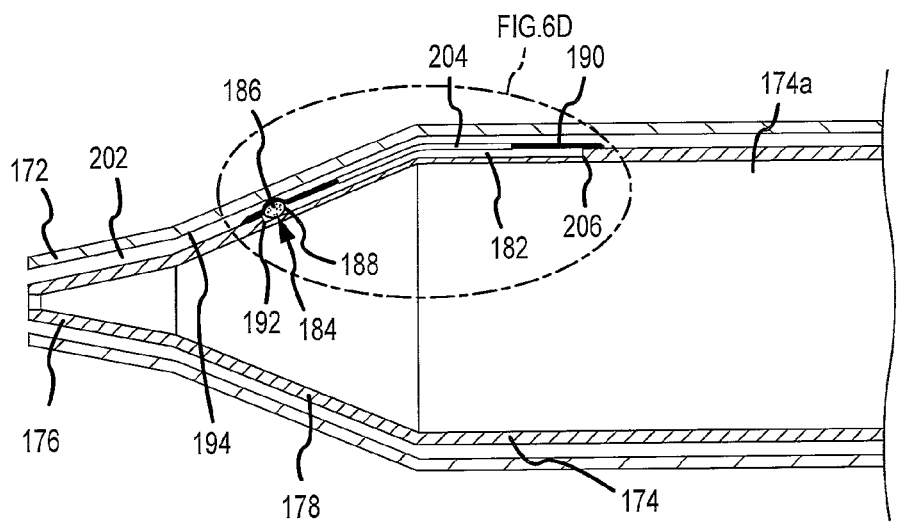
FIG. 6C is a partial, enlarged, cross-sectional view of the syringe of FIG. 6A in a first state.
Figure 6D:
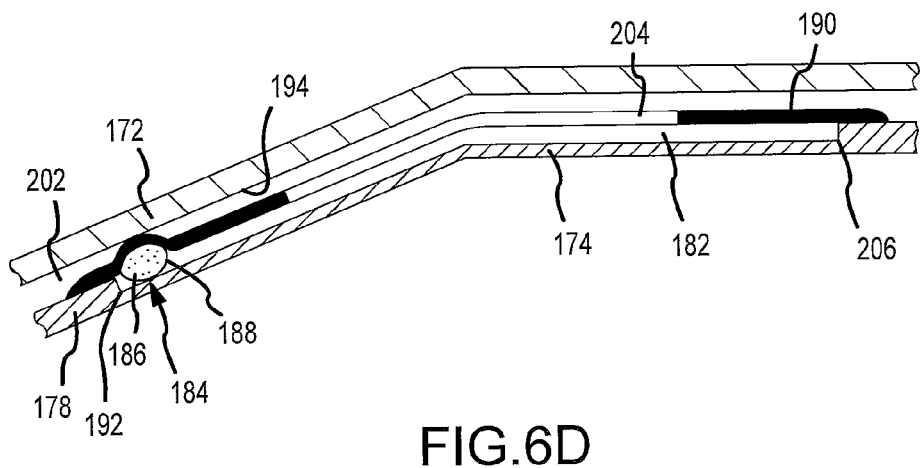
FIG. 6D is a detailed view of a portion of the syringe of FIG. 6C.
Figure 6E:
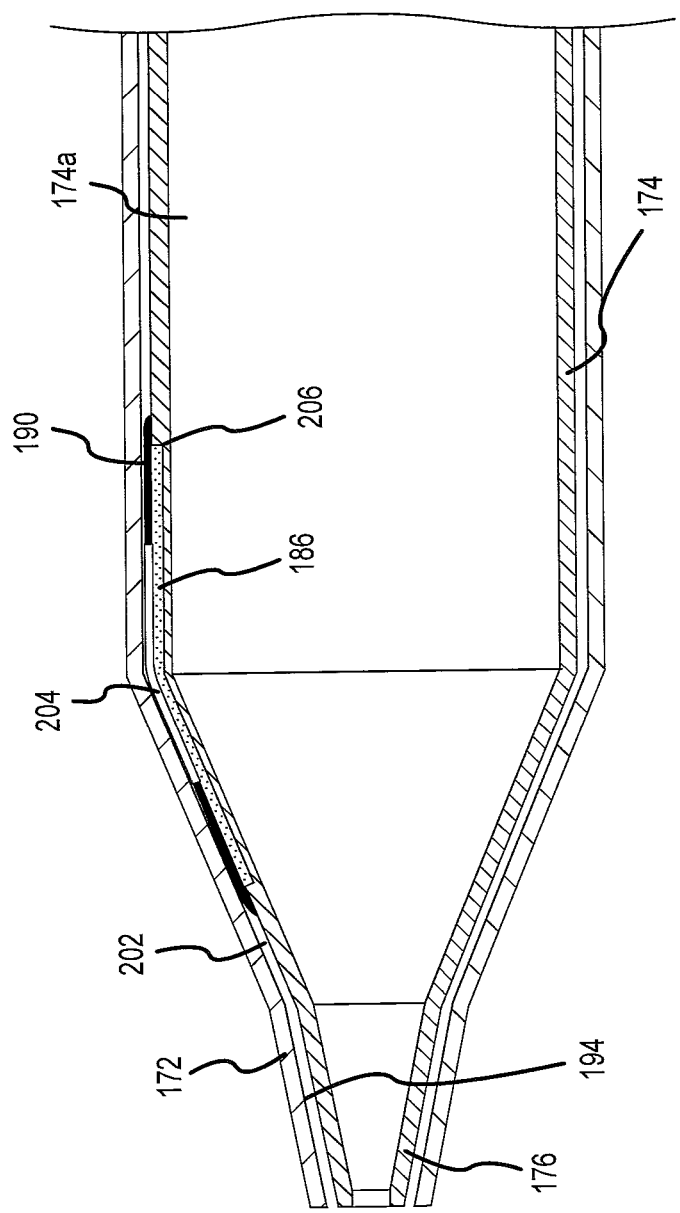
FIG. 6E is a partial, enlarged, cross-sectional view of the syringe of FIG. 6A in a second state.

Like the syringes 110, 140 discussed above, the syringe 170 may interact with the syringe plunger driver assembly 56 (FIG. 2C) of the power injector 40 (FIGS. 2A-C) through a syringe plunger coupler 196 of a syringe plunger 198. When disposed in interacting relation, the syringe plunger driver assembly 56 (FIG. 2C) advances the syringe plunger 198 relative to the syringe body 174 so as to discharge fluid from the nozzle 176. The resulting pressure within the syringe 170 may cause the conical transition portion 178 of the syringe 170 to distort, the syringe 170 to move axially relative to the pressure jacket 172, or both, and as a result, the enclosed fluid source 184 is pressed between the exterior of the conical transition portion 178 and an inside surface 194 of the pressure jacket 172, thereby rupturing the enclosed fluid source 184 and releasing the indicator fluid 186 to flow from the proximal end 192 of the channel 182 to a distal end 206 of the channel 182, as shown in FIGS. 6C and 6E.

In this embodiment, the label 190 may include a transparent portion 204 that extends at least from the proximal end 192 of the channel 182 to the distal end 206 of the channel 182, such that an operator may observe the indicator fluid 186 present in the channel 182 and know that the syringe 170 has been previously discharged. To allow for prominent visual indication, the indicator fluid 186 may be any colored fluid of an appropriate viscosity that allows the indicator fluid 186 to flow along the channel 182 once the enclosed fluid source 184 has ruptured.

Figure 7:
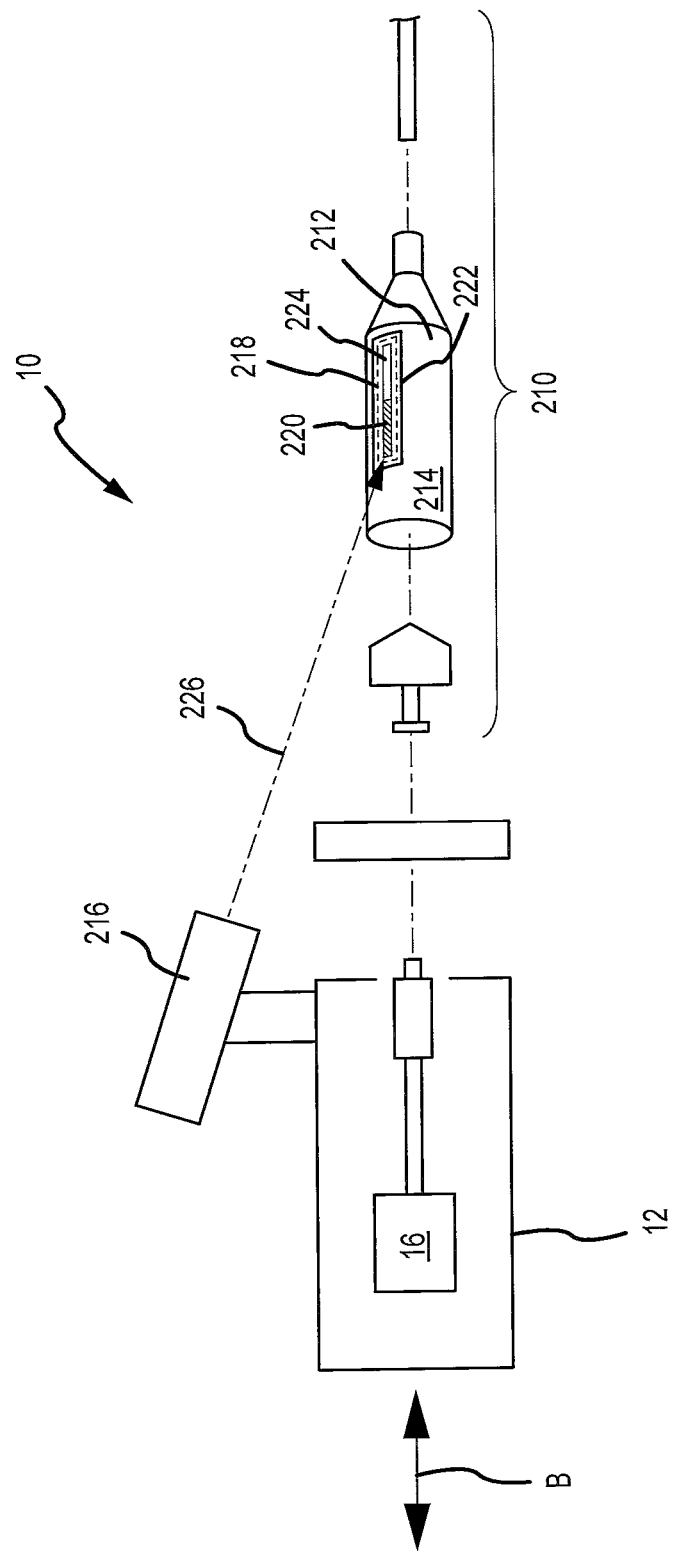
FIG. 7 is a schematic of a syringe for a power injector that utilizes another embodiment of a visual indicator.

Another embodiment of a syringe 210 for installation on and use with a power injector is illustrated in FIG. 7. Hereafter, the syringe 210 will be described in conjunction with the power injector 10 (FIG. 1) although it should be appreciated that the syringe 210 may be used with any appropriate power injector (e.g., the power injector 40 of FIGS. 2A-C). Generally, the visual indicator used by the syringe changes states (e.g., colors) when exposed to light of a certain wavelength or within a wavelength range. In one embodiment, an ultraviolet (UV) light source is utilized and the syringe 210 will be discussed with regard to the same. Other light sources may be appropriate.

In the FIG. 7 embodiment, a section of material that is sensitive to ultra violet ("UV") light, or a section of UV-sensitive material 220, may be disposed between an exterior surface 214 of a syringe body 212 and a label 222 that is at least partially transparent. The UV-sensitive material 220 may be in the form of any material that exhibits an optically-detectable response to exposure to UV light (e.g., UV-sensitive adhesives, gels, foams, paints, etc.). For example, the section of UV-sensitive material 220 may change from a first color to a second color when exposed to UV light.

To activate the section of UV-sensitive material 220, the powerhead 12 (FIG. 1) may incorporate a UV light source 216 in any appropriate manner that positions the UV light source 216 in a way that when flashed, the section of UV-sensitive material 220 on the syringe body 212 is directly exposed to a stream of UV light 226 (e.g., the light source 216 may be fixably or detachably mounted to the powerhead 12 via fasteners, clamps, straps, adhesive, etc.). It should also be appreciated that the UV light source 216 may be interconnected with other components of the power injector 10 or any other appropriate surface or structure. In one embodiment, the light source 216 may be a handheld unit. During an injection procedure, the UV light source 216 may flash before or after the power injector discharges fluid from the syringe 170, thereby exposing the section of UV-sensitive material 220 to UV light and causing it to transition from a first state to a second state (e.g., from a first color to a second color). In this regard, the UV light source 216 may be manually activated or activation may be integrated with an automatic injection or operations protocol such that the powerhead 12 controls the UV light source 216 (e.g. control logic may activate the light source 112 when the ram 20 is advanced).

In one embodiment, the label 222 may be any appropriate size or shape that is sufficient to fully contain the section of UV-sensitive material 220 between the label 222 and the exterior surface 214 of the syringe body 212. Specifically, beyond an offset perimeter 218, the label 222 may affix directly to the exterior surface 214 of the syringe body 212 so as to fully contain the section of UV-sensitive material 220 within the offset perimeter 218, as shown in FIG. 7. It should be appreciated that in other embodiments, the offset perimeter 218 will be unnecessary. For example, in one embodiment, the section of UV-sensitive material 220 may be in the form of a label adhesive that has been treated with UV-sensitive additives. In this embodiment, the section of UV-sensitive material 220 may span the full area beneath the label 222, which may be partially or fully transparent to allow some or all of the adhesive to show through the label 222. If the label 222 is not completely transparent, it may include at least a transparent portion 224 through which the section of UV-sensitive material 220 is visible to an operator who may observe the section of UV-sensitive material 220 both before and after the syringe 210 is exposed to UV light during an injection procedure. The transparent portion 224 may be any appropriate shape or size to maximize visibility.

The various syringes disclosed herein may be used in conjunction with power injectors as noted. They may be appropriate for use with other injection devices as well. For instance, each of the syringes disclosed herein may be used with the type of hand-held, hand-powered injectors of the type disclosed by U.S. Pat. No. 7,041,084, entitled "HAND-HELD, HAND OPERATED POWER SYRINGE AND METHODS," and that issued on May 9, 2006.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:
1. A syringe, comprising:
   a syringe body that defines an internal fluid discharge chamber and that comprises a movable member exposed to pressure within said internal fluid discharge chamber;
   a syringe plunger movably disposed within said syringe body; and
   a fluid source disposed outside of said fluid discharge chamber, wherein said movable member is aligned with said fluid source, wherein said movable member moves in response to pressurization within said internal fluid discharge chamber generated b movement of said syringe plunger relative to said syringe body, and wherein movement of said movable member releases a first fluid from said fluid source to provide a visual indication that fluid has been discharged from said syringe body.

2. The syringe of claim 1, wherein said fluid source comprises an enclosure, wherein said first fluid is contained within said enclosure.

3. The syringe of claim 2, wherein said enclosure is a deformable member.

4. The syringe of claim 2, wherein said enclosure ruptures upon exposure to at least a certain pressure.

5. The syringe of claim 2, wherein said enclosure comprises a blister pack.

6. The syringe of claim 1, further comprising a flowpath fluidly interconnectable with said fluid source.

7. The syringe of claim 6, wherein said fluid source and said flowpath are fluidly isolated when said syringe is in a first state, and wherein said fluid source communicates with said flowpath when said syringe is in a second state.

8. The syringe of claim 7, wherein said first state is prior to an advancement of said syringe plunger to discharge fluid from said syringe body, and wherein said second state is a development of a differential pressure in response to an advancement of said syringe plunger to discharge fluid from said syringe body.

9. The syringe of claim 6, wherein an exterior surface of said syringe body comprises a channel, and wherein said channel comprises said flowpath.

10. The syringe of claim 9, wherein said channel extends at least about 10% of a length of said syringe body.

11. The syringe of claim 9, further comprising a label disposed over said channel.

12. The syringe of claim 1, wherein said movable member moves from a first position to a second position in response to a differential pressure that develops by advancement of said syringe plunger.

13. The syringe of claim 12, wherein said first fluid is released from said fluid source in response to said movable member moving from said first position to said second position.

14. The syringe of claim 1, wherein said movable member comprises a dimple.

15. The syringe of claim 14, wherein said dimple inverts in response to movement of said syringe plunger.

16. The syringe of claim 14, wherein said dimple is convex on an interior of said syringe and is concave on an exterior of said syringe prior to movement of said syringe plunger in a direction to discharge fluid from said syringe.

17. The syringe of claim 16, wherein movement of said syringe plunger in a direction to discharge fluid from said syringe inverts said dimple so that said dimple is concave on said interior of said syringe and is convex on said exterior of said syringe.

18. The syringe of claim 14, wherein inversion of said dimple in response to movement of said syringe plunger ruptures said fluid source.

19. The syringe of claim 1, wherein said movable member comprises a deformable section of said syringe.

20. The syringe of claim 1, wherein said syringe body comprises a barrel and a discharge port, and wherein said fluid source is located between said barrel and said discharge port.

21. The syringe of claim 1, wherein said syringe comprises a frustumly-shaped surface, and wherein said fluid source coincides with said frustumly-shaped surface.

22. The syringe of claim 1, wherein said first fluid of said fluid source comprises a colored liquid.

* * * * *

UNITED STATES PATENT AND TRADEMARK OFFICE
CERTIFICATE OF CORRECTION

| | |
|---|---|
| PATENT NO. | : 8,983,579 B2 |
| APPLICATION NO. | : 13/794141 |
| DATED | : March 17, 2015 |
| INVENTOR(S) | : Kevin R. Martz |

It is certified that error appears in the above-identified patent and that said Letters Patent is hereby corrected as shown below:

In the claims,

At Column 20, line 65 (line 11 of claim 1), delete "b" and insert therefore --by--.

Signed and Sealed this
Twenty-first Day of July, 2015

Michelle K. Lee
*Director of the United States Patent and Trademark Office*